United States Patent [19]

Taylor

[11] Patent Number: 5,373,094
[45] Date of Patent: Dec. 13, 1994

[54] REACTIVE DYES CONTAINING A 2,6-DIFLUORO-3,5-DICHLOROPYRIDINE GROUP

[75] Inventor: John A. Taylor, Manchester, United Kingdom

[73] Assignee: Zeneca Limited, London, United Kingdom

[21] Appl. No.: 80,724

[22] Filed: Jun. 24, 1993

[30] Foreign Application Priority Data

Jun. 25, 1992 [GB] United Kingdom ............... 9213475

[51] Int. Cl.[5] .................... C09B 62/002; C09B 62/04; C09B 62/36; D06P 1/382
[52] U.S. Cl. ........................ 534/618; 534/630; 534/632; 540/124; 540/126; 544/76; 544/189; 546/285
[58] Field of Search ............... 534/618, 630, 632; 544/76, 189; 540/124, 126; 546/285

[56] References Cited

U.S. PATENT DOCUMENTS

| | | | |
|---|---|---|---|
| 3,915,951 | 10/1975 | Agback et al. | 534/664 |
| 4,213,899 | 7/1980 | Phillips et al. | 534/630 |

FOREIGN PATENT DOCUMENTS

| | | | |
|---|---|---|---|
| 1122389 | 8/1968 | United Kingdom | 534/630 |
| 1555423 | 11/1979 | United Kingdom | . |
| 2063284 | 6/1981 | United Kingdom | . |

OTHER PUBLICATIONS

Moran et al., J. Chem. Soc., Perkin Trans. I, (20), pp. 2310–2313, 1974.

*Primary Examiner*—Patricia L. Morris
*Assistant Examiner*—Fiona T. Powers
*Attorney, Agent, or Firm*—Cushman, Darby & Cushman

[57] ABSTRACT

A water-soluble dye which contains a group of Formula (1):

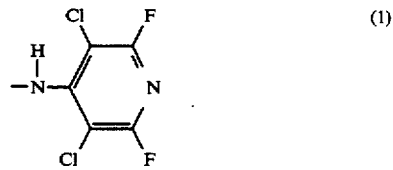

(1)

The dyes of Formula (1) can be used to dye materials including natural and artificial textile materials such as wool, silk, polymides and modified polyacrylonitrile fibers.

5 Claims, No Drawings

REACTIVE DYES CONTAINING A 2,6-DIFLUORO-3,5-DICHLOROPYRIDINE GROUP

This invention relates to dyes which contain a 2,6-difluoro-3,5-dichloropyridin-4-ylamino reactive group of Formula (1) (hereinafter a DFDC group), to a process for their manufacture, to a process for the coloration of materials using the dyes and to materials when coloured by the dyes.

According to the present invention there is provided a water-soluble dye which contains a group of the Formula (1):

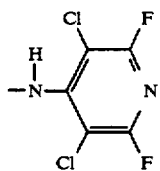

It is preferred that the DFDC group is attached to an aromatic carbon atom in the dye, that is to say a carbon atom which is part of an aromatic ring, for example a carbon atom of a phenyl or naphthyl ring.

Preferably the water-soluble dye according to the invention contains 1, 2 or 3 DFDC groups. Preferred dyes according to the invention contain at least two, more preferably at least 3 and preferably less than 11 sulpho groups.

A preferred dye according to the invention contains a group of the Formula (2):

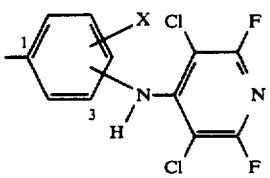

wherein:

X is H or sulpho.

It is preferred that the DFDC group is at the 3-position as shown in Formula (2).

In addition to the DFDC group the dye may contain a different reactive group, preferably a pyrimidinyl amino group, or more preferably a vinyl sulphone or triazinylamino reactive group.

The pyrimidinylamino reactive group is preferably halopyrimidinylamino, especially trichloropyrimidinylamino, and more especially a difluorochloropyrimidinylamino group.

The term vinyl sulphone group includes vinyl sulphonyl and groups which are convertible to vinyl sulphonyl in the presence of aqueous alkali, for example —CH$_2$CH$_2$OSO$_3$H and —CH$_2$CH$_2$SSO$_3$H.

The triazinylamino reactive group is preferably a 2,4,6-s-triazinylamino group carrying a labile atom or group at the 3-position and, at the 5-position, a labile atom or group, an alkoxy group, especially C$_{1-4}$-alkoxy or an optionally substituted alkyl group, especially optionally substituted phenylamino or optionally substituted alkylamino. Preferred optional substituents are selected from sulpho and DFDC. The preferred optionally substituted alkylamino group is an optionally substituted C$_{1-4}$-alkylamino group, for example CH$_3$—NH— and CH$_3$CH$_2$—NH—.

Accordingly a further preferred dye according to the invention contains a group of the Formula (3):

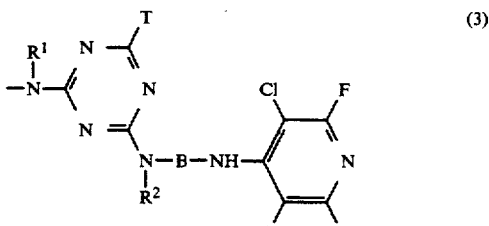

wherein:

R$^1$ & R$^2$ are each independently H or C$_{1-4}$-alkyl;

T is a labile atom or group; and

B is an optionally substituted alkylene, phenylene or naphthylene group.

The optional substituent which may be present on B is preferably hydroxy, amino or especially sulpho.

A preferred optionally substituted alkylene group represented by B is a C$_{2-4}$-alkylene group, especially —CH$_2$CH$_2$—. When B is optionally substituted phenylene or naphthylene it preferably carries a sulpho group. A preferred phenylene group is a phen-1,3-ylene group, especially sulphophen-1,3-ylene.

By a labile atom or group, it is meant an atom or group which is bound by a chemical bond to the triazine nucleus, which atom or group is displaceable by a hydroxyl group of cellulose under mildly alkaline aqueous conditions to form a covalent bond between the triazine nucleus and cellulose. As examples of such atoms or groups, there may be mentioned halogen atoms such as F and Cl; sulphonic acid groups; thiocyano groups; quaternary ammonium groups such as trialkylammonium groups; and optionally substituted pyridinium groups such as nicotinyl and iso-nicotinyl groups. It is preferred that T is halo, especially fluoro or chloro; or 3- or 4-carboxypyridinium.

The water-soluble dye according to the invention is preferably a water-soluble azo, anthraquinone, phthalocyanine, triphenodioxazine or formazan dye. Thus preferred dyes of the present invention are of the formula D—(Z)$_n$ wherein Z is of Formula (1), (2) or (3) as hereinbefore defined, n is 1, 2 or 3 and D is the residue of an azo, anthraquinone, phthalocyanine, triphenodioxazine or formazan chromophore. Examples of groups represented by D are given in the following pages in Formulae (4) to (11) wherein D is the portion of the illustrated molecules other than group Z.

Preferred water-soluble azo dyes are monoazo and diazo dyes.

Preferred monoazo dyes are formula L—N=N—L$^1$—Z wherein L is an aryl or heteroaryl radical, L$^1$ is an arylene radical and Z is of Formula (1), (2) or (3) as hereinbefore defined.

It is preferred that each aryl or arylene radical independently is a mono- or di-cyclic aryl or arylene radical. Preferred aryl radicals are optionally substituted phenyl and naphthyl, and preferred arylene radicals are phenylene and naphthylene. Preferred heteroaryl radicals are pyridonyl and pyrazolony.

A first preferred monoazo dye is of the Formula (4) or salt thereof:

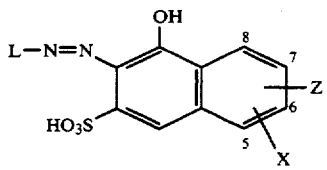

(4)

wherein:

L, X and Z are as hereinbefore defined.

L is preferably optionally substituted phenyl or naphthyl, especially a phenyl or naphthyl group having at least one sulpho substituent. Further optional substituents which may be present on L include a halogen atom, especially chlorine; an alkyl radical, especially $C_{1-4}$-alkyl, more especially methyl; an acylamino radical, especially acetylamino, benzamido or sulphonated benzamido; amino; hydroxy; and an alkoxy radical, especially $C_{1-4}$-alkoxy, more especially methoxy.

As examples of phenyl groups having at least one sulpho substituent there may be mentioned 2-, 3- or 4-sulphophenyl; 2-sulpho-4-nitrophenyl; 2-sulpho-5-nitrophenyl; 4-sulpho-2-methylphenyl; 5-sulpho-2-methylphenyl; 2-sulpho-4-methylphenyl; 5-sulpho-2-methoxy phenyl; 2-sulpho-4-methoxyphenyl; 4-sulpho-2-chlorophenyl; 5-sulpho-2-carboxyphenyl; 2,4-disulphophenyl; 2,5-disulphophenyl; and 3,5-disulphophenyl.

As examples of naphthyl groups having at least one sulpho substituent there may be mentioned 1-sulphonaphth-2-yl; 1,5,7-trisulphonaphth-2-yl; 3,6,8-trisulphonaphth-2-yl; 5,7-disulphonaphth-2-yl; 6-sulphonaphth-2-yl; 4-, 5-, 6- or 7-sulphonaphth-1-yl; 4,8-disulphonaphth-1-yl; 3,8-disulphonaphth-1-yl; 2,5,7-trisulphonaphth-1-yl; and 3,5,7-trisulphonaphth-1-yl.

Preferred optional substituents which may be present on $L^1$ are those mentioned above for L.

In dyes of Formula (4) Z is preferably at the 6-, 7- or 8-position, especially the 6- or 8-position. When Z is at the 8-position it is preferred that X is a sulpho group and is at the 5- or 6-position.

A second preferred monoazo dye is of the Formula (5) or a salt thereof:

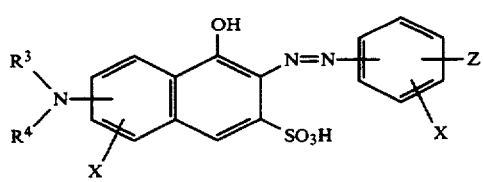

(5)

wherein:

$R^3$ is H or $C_{1-4}$-alkyl;

$R^4$ is H, $C_{1-4}$-alkyl; $C_{1-4}$-alkanoyl; optionally substituted benzoyl, especially benzoyl or sulphobenzoyl, acetyl, propanoyl, n-butanoyl or iso-butanoyl; and Z and each X is as hereinbefore defined.

A third preferred monoazo dye is of the Formula (6) or salt thereof:

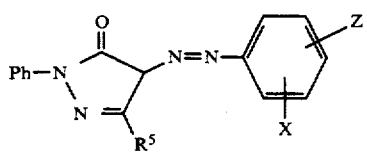

(6)

wherein:

Ph is an optionally substituted phenyl group, especially sulphophenyl;

$R^5$ is CN, $CH_3$ or carboxy; and

X and Z are as hereinbefore defined.

A preferred diazo dye is of Formula (7) or salt thereof:

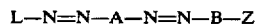

$$L-N=N-A-N=N-B-Z \qquad (7)$$

wherein:

A and B are each independently optionally substituted phenylene or naphthylene; and L and Z are as hereinbefore defined.

It is preferred that B is optionally substituted phenylene and A is optionally substituted naphthylene. The optional substituents which may be present on A or B are preferably independently selected from halo, especially chloro; alkoxy, especially $C_{1-4}$-alkoxy; alkyl, especially methyl; sulpho; carboxy; hydroxy; amino; acylamino such as acetamido, benzamido and sulphonated benzamido; hydroxy; and a pyrimidinylamino or triazinylamino cellulose-reactive group or a group of Formula (1) or (3) as hereinbefore defined.

As Examples of groups represented by A and B there may be mentioned phenylene, sulphophenylene, ureidophenylene, 5-sulpho-1,4-naphthylene, 6-sulpho-1,4-naphthylene and 8-sulpho-1,4-naphthylene.

A preferred anthraquinone dye is of the Formula (8) or a salt thereof:

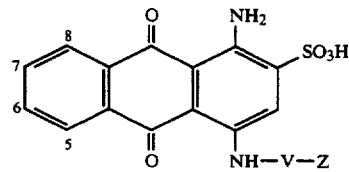

(8)

wherein the anthraquinone nucleus optionally contains a sulphonic acid group in the 5-, 6-, 7- or 8-position and V is a divalent organic linking group, preferably of the benzene series. V is preferably phenylene, diphenylene, or 4,4'-divalent stilbene or azobenzene radicals which are optionally sulphonated. It is preferred that V contains one sulphonic acid group for each benzene ring present.

A preferred phthalocyanine dye is of the Formula (9) or a salt thereof:

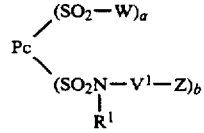

(9)

wherein Pc is a metallo-phthalocyanine nucleus, preferably copper or nickel phthalocyanine; $R^1$ is as hereinbefore defined; each W independently is a hydroxy or a substituted or unsubstituted amino group, $V^1$ is a divalent organic linking group, preferably a $C_{1-4}$-alkylene or phenylene linking group; and a and b are each independently 1, 2 or 3 provided that a+b is not greater than 4.

A preferred triphenodioxazine dye is of the Formula (10) or a salt thereof:

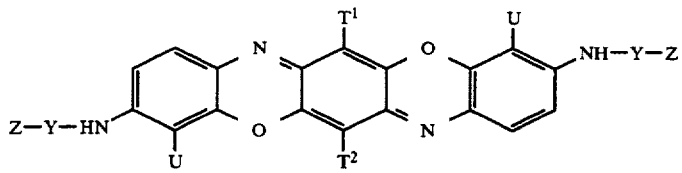

(10)

wherein:
each
Y independently is a covalent bond, $C_{2-4}$-alkylene, phenylene or sulphophenylene;
U is H or $SO_3H$;
$T^1$ and $T^2$ are halo, especially chloro, $C_{1-4}$-alkyl, or $C_{1-4}$-alkoxy; and each Z independently is as hereinbefore defined.
Each Y is preferably $-C_2H_4-$ or $-C_3H_6-$, U is preferably $SO_3H$, and
$T^1$ and $T^2$ are preferably Cl or methyl.

It is preferred that both groups represented by Z in Formula (10) are identical to each other.

A preferred formazan dye is of the Formula (11) or a salt thereof:

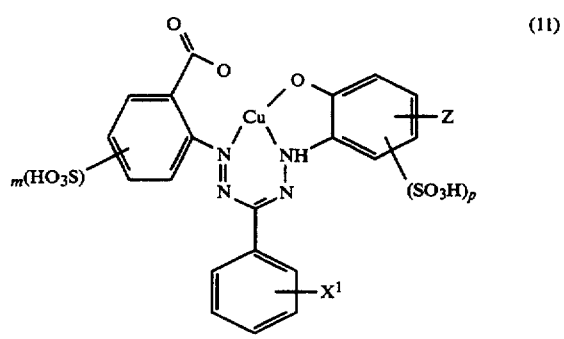

(11)

wherein:
$X^1$ is H, $SO_3H$ or Cl;
m and p each independently have a value of 0, 1 or 2; and
Z is as hereinbefore defined; provided that the formazan group has at least one, and preferably at least two, sulpho groups.

It is preferred that m and p each have a value of 1.

In dyes of Formula (4) to (11) it is preferred that Z is of Formula (1) or (3).

Dyes according to the invention may be prepared by a process comprising condensation of 2,4,6-trifluoro-3,5-dichloropyridine and a dye having an $-NH_2$ group, preferably in a liquid medium. It is preferred that the condensation is performed at 10°-90° C., especially 20°-90° C., more especially 40°-90° C. The liquid medium is preferably an aqueous medium or comprises dimethylsulphoxide.

The condensation is preferably performed in the presence of an acid-binding agent. The function of the acid-binding agent is to neutralise hydrogen fluoride as it is formed during the condensation. Accordingly any acid-binding agent may be used provided that it is not present in such a concentration that it causes hydrolysis of the reactants or causes some other side-reaction. It is preferred to use an alkali metal hydroxide, carbonate or bicarbonate, added at such a rate that the pH of the mixture stays within the range of 5.0 to 6.0.

According to a further aspect of the present invention there is provided a compound of the Formula (12) and use thereof for the preparation of a dye:

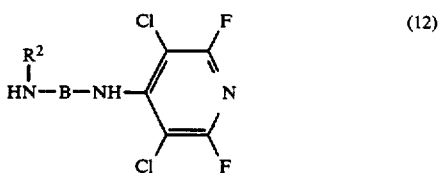

(12)

wherein:
$R^2$ and B are as hereinbefore defined.

In a compound of Formula (12) B is preferably $C_{2-4}$-alkylene, optionally substituted phenylene, more preferably optionally substituted phen-1,3-ylene, wherein the optional substituents are as hereinbefore described for B.

A compound of Formula (12) wherein $R^2$ is H or $C_{1-4}$-alkyl may be used to prepare a dye containing a group of Formula (3) by condensation with a dye having a dihalotriazinylamino substituent or with a dye having an atom or group which is displaceable by nucleophilic substitution. Condensation is preferably performed in an aqueous solvent, more preferably at 20°-90° C. It is preferred that the condensation is performed in the presence of an acid binding agent.

A compound of Formula (12) wherein $R^2$ is H and B is an optionally substituted phenylene or naphthylene group is also useful as a diazotisable amine which may be coupled with a coupling component to give an azo dye. Diazotisation may be achieved by treating a solution of the compound of Formula (12) with sodium nitrite and hydrochloric acid at below 5° C.

A compound of Formula (12) may be prepared by condensing 2,4,6-trifluoro-3,5-dichloropyridine with diamine of formula $HN(R^2)$—B—$NH_2$, preferably in dimethylsulphoxide at 20°-90° C., wherein $R^2$ and B are as hereinbefore defined.

Although dye formulae have been shown in the form of their free acid in this specification, the invention also relates to the dyes in the salt form, particularly their salts with alkali metals such as the sodium, lithium or mixed sodium/lithium salt.

A further feature of the present invention provides a composition comprising an inert carrier and a water-soluble reactive dye according to the invention, preferably in a weight ratio of 1:99 to 99:1, more preferably 50:1 to 1:50, especially 20:1 to 1:20. The inert carrier preferably comprises inorganic salts and optionally a de-dusting agent. Examples of inorganic salts include alkali and alkali earth metal halides, carbonates, bicarbonates, nitrates and mixtures thereof. Dodecylbenzene may be used as a de-dusting agent.

The present invention also provides a process for the coloration of a substrate comprising applying thereto a dye according to the present invention, preferably in aqueous solution.

The reactive dyes of the present invention are suitable for colouring natural and artificial textile materials containing amino or hydroxyl groups, for example textile materials such as wool, silk, polyamides and modified polyacrylonitrile fibres, and more especially cotton, viscose rayon and other regenerated cellulosic materials. For this purpose the dyes can be applied to the textile materials by exhaust dyeing, or by padding or by printing using printing pastes containing the conventional thickening agents or oil-in-water emulsions, whereby the textile materials are coloured bright shades and possess good fastness to light and to wet treatments such as washing and also possess good wash off.

The new dyes are particularly valuable for colouring cellulosic textile materials. For this purpose the dyes are preferably applied to the cellulosic textile material in conjunction with a treatment with an acid-binding agent, for example, sodium bicarbonate, sodium carbonate, sodium metasilicate, trisodium phosphate or sodium hydroxide, which may be applied to the cellulose textile material before, during or after the application of the dye.

The new dyes can be applied to textile materials containing amino groups, such as wool and polyamide textile materials, from a mildly alkaline, neutral or acid dyebath. The dyeing process can be carried out at a constant or substantially constant pH, that is to say the pH of the dyebath remains constant or substantially constant during the dyeing process, or if desired the pH of the dyebath can be altered at any stage of the dyeing process by the addition of acids or acid salts or alkalis or alkaline salts.

In a preferred aspect of the present invention the new dyes are applied to a textile material by printing, for example including ink jet printing.

The invention is illustrated but not limited by the following Examples in which all parts and percentages are by weight unless stated otherwise.

EXAMPLE 1

Preparation of

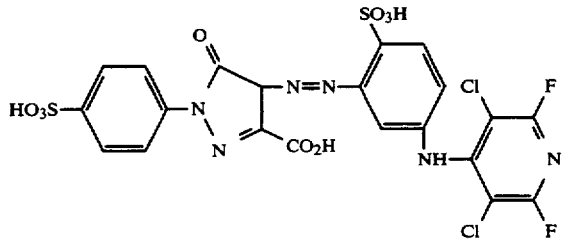

A solution of the diazonium salt of 2-amino-4-(2,6-difluoro-3,5-dichloropyridin-4-yl)aminobenzene sulphonic acid (0.01M) at below 5° C. was added to a stirred solution of 1-(4-sulphophenyl)-3-carboxypyrazol-5-one (2.8g, 0.01M) at pH 2.0. The pH was raised slowly to 6.5 with 2N sodium carbonate solution and the temperature was allowed to raise to 20° C. After 1 hour salt solution (20% w/v) was added and the precipitated title product was collected. The structure of the title product was confirmed by $^1$H NMR spectroscopy in DMSO. Signals were observed at (delta) 8.7, 9.78, 6.68, 7.78, 16.38, 7.78 and 8.1 ppm.

Yield 6.6 g, M.I. 1667, 40%.

A piece of woven cotton printed with title dye was found to have a bright greenish yellow shade.

Example 2

Preparation of

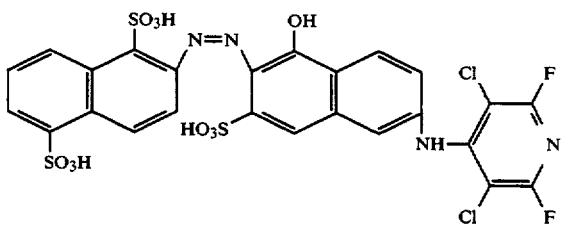

2N Sodium nitrite (38 ml, 0.016M) was added to a stirred suspension of 2-aminonaphthalene-1,5-disulphonic acid (0.067M) at 0° C. and pH 2.0. After 1 hour excess nitrous acid was destroyed (sulphamic acid) and the resulting diazonium salt was added to a solution of 1-hydroxy-6-(2,6-difluoro-3,5-dichloropyridin-4-yl)amino naphthalene-3-sulphonic acid (0.06M) in water at pH 6.0. After coupling the title product was precipitated by the addition of ethanol.

Yield 19.5 g, M.I. 1319, 25%.

$^{19}$F NMR showed a single peak at −72.9 ppm, consistent with the above para isomer of DFDC. $^1$H NMR (DMSO-$d_6$, delta) showed signals at 7.45, 7.9, 9.18, 8.98, 8.78, 16.28, 7.42, 7.16, 8.2, 7.2 and 9.8 ppm.

The title product was printed on cotton under standard conditions to give a bright orange print.

The title product was also applied to cotton by exhaust dyeing from a dyebath containing salt and sodium carbonate and was found to give strong orange dyeings.

EXAMPLE 3

Preparation of a dye of Formula (13) wherein D$^1$ is 1-hydroxy-8-benzoyl amino-3,6-disulphonaphth-2-yl

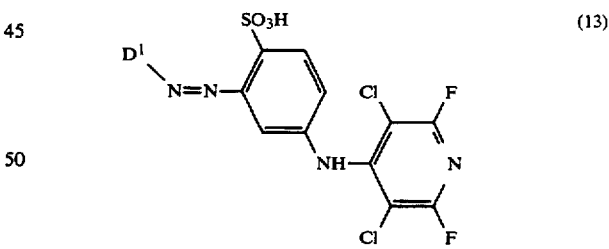

(13)

Stage (a)

2,4,6-trifluoro-3,5-dichloropyridine was added to a solution of 1,4-diaminobenzesulphonic acid in water at 45° C. and pH 5.5 until reaction was complete. The product, 2-amino-4-(2,6-difluoropyridin4-yl)aminobenzene sulphonic acid, was used in stage (b) without intermediate isolation.

Stage (b)

A solution of 2-amino-4-(2,6-difluoro-3,5-dichloropyridin-4-yl)aminobenzene sulphonic acid (0.01 m) was stirred in water at pH 2.0 and 0° to 5° C. whilst 2N sodium nitrite (5 ml, 0.011M) was added slowly with stirring. After 30 minute excess nitrous acid was destroyed and a solution of 1-hydroxy-8-benzoylaminonaphthalene-3,6-disulphonic acid (0.01M) was added, the mixture was stirred at pH 6.0 and allowed to warm to 20° C. Salt was added and the title product was collected.

Yield 14.7 g, M.I. 2340, Yield 64%.

The title product was examined by negative ion fast atom bombardment mass spectometry. An isotopic cluster (2Cl, 35) at m/z 802 corresponding to (M-H)$^-$, consistent with the title product was observed. Additionally isotopic clusters at m/z 824 and 846 corresponding to Na and Na$_2$ salts were observed.

The title product was mixed with sodium carbonate, sodium alginate thickener and auxiliary chemicals and printed onto woven cotton fabric to give a bright red print with good fastness properties.

EXAMPLE 4

Preparation of a dye of Formula (13) wherein $D^1$ is 1-hydroxy-6-acety amino-3-sulphonaphth-2-yl A solution of the diazonium salt of 2-amino-4-(2,6-difluoro-3,5-dichloropyridin-4-yl)aminobenzene sulphonic acid (0.01M) prepared as in Example 1 was added to a solution of 1-hydroxy-6-acetylaminonaphthalene-3-sulphonic acid (0.01M, 3.92 g). After stirring at pH 6.5 and 20° C. for 1 hour precipitated solid [?]was collected and dried. The structure of the title product was confirmed by $^1$H NMR spectroscopy in DMSO-d$_6$ as solvent. Signals (delta) were observed at 6.58, 7.68, 7.58, 15.58, 7.3, 7.78, 8.28, 7.78, 9.38 and 2.28 ppm.

Yield 7.5 g, M.I. 958, 78%.

The title product was made into a print paste with water, sodium alignate thickener and sodium carbonate and printed onto cotton. The cotton was steamed for 10 minutes to give a bright greenish orange print.

EXAMPLE 5

Preparation of a dye of Formula (13) wherein $D^1$ is 1-hydroxy-8-amino-7-(2,5-disulphophenylazo)-3,6-disulphonaphth-2-yl 2-Amino-4-(2,6-difluoro-3,5-dichloropyrid-4-yl)aminobenzene sulphonic acid (7.4 g, 0.02M) was added to a stirred mixture of water (50 g), ice (50 g) and concentrated hydrochloric acid (10ml) followed by 2N sodium nitrite. After stirring at 0° C. for 90 minutes a few drops of 10% sulphamic acid were added and the resulting diazonium salt suspension was added portionwise at 0° C. to 5° C. and pH 7 to a solution of 1-amino-2-(2,5-disulphophenylazo-)-8-hydroxynaphthalene-3,6-disulphonic acid (0.012M) until all of the diazonium salt had been consumed (this required approximately 0.015M of diazonium salt). The solution was allowed to warm to room temperature, evaporated to small volume under reduced pressure and ethanol added to the concentrated solution. The resulting precipitated title product was collected.

Yield 14.6 g, M.I. 1675, 73%.

The title product showed $^1$H NMR signals (delta, DMSO-d$_6$) at 7.98, 7.66, 8.16, 7.4, 15.78, 7.75, 7.65 and 6.85 ppm. $^{19}$F NMR showed a single peak at $-73.3$ ppm.

The title product was found to print woven cotton a heavy navy shade.

EXAMPLE 6

Preparation of a dye of Formula (13) wherein $D^1$ is 1-hydroxy-4-sulphonaphth-2-yl 2-Amino-4-(2,6-difluoro-3,5-dichloropyridin-4-yl)aminobenzene sulphonic acid (15.36 g, 0.044M) was added to a stirred mixture of water (100 g), ice (50 g), and concentrated HCl (0.2M) followed by 2N sodium nitrite (22 ml, 0.044M). After stirring at 0° C. for 90 minutes a few drops of 10% Sulphamic acid were added to destroy any excess HNO$_2$. A solution of 1-Naphthol-4-Sulphonic acid was added at pH 7 (1.75 g, 0.012M) and 0°–5° C. The reaction proceeded at 0°–5° C., pH 2, until all the diazonium salt had been consumed, the title product precipitated out of solution and was filtered off.

Yield 10 g

EXAMPLE 7

Preparation of a dye of Formula (13) wherein $D^1$ is 1-hydroxy-8-amino-7-(4-betasulphatoethylsulphonylphenylazo)-3,6-disulphonaphth-2-yl 2-Amino-5-(2,6-difluoro-3,5-dichloropyridin-2-ylamino)benzene sulphonic acid (0.035M) was added to 7 ml of cold hydrochloric acid (12N) in water (120 ml) followed by dropwise addition of 2N sodium nitrite solution (20 ml), with stirring, at 0° C. to 5° C. After 30 minutes excess nitrous acid was destroyed using sulphamic acid and the resultant mixture of diazonium salt was added to a solution of 1-amino-2-[4-beta sulphatoethylsulphonylphenylazo]-8-hydroxynaphthalene-3,6-disulphonic acid (0.028M) whilst maintaining the pH at 6.5. After 2 hours at 0° C. to 5° C. and pH 6.5 coupling was essentially complete. Salt (17.5% w/v) was added slowly with stirring and the resultant precipitated product collected.

Yield 41 g.

EXAMPLE 8

Preparation of a dye of Formula (14) wherein $D^2$ is 1-hydroxy-2-(1-sulpho naphth-2-ylazo)-3,6-disulphonaphth-8-yl

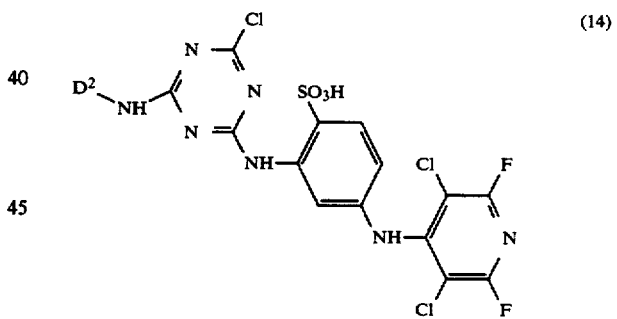

2-Amino-4-(2,6-difluoro-3,5-dichloropyridin-4-yl)aminobenzene sulphonic acid (5.13 g, 0.011M) was added at 35° C. and pH 6.5 to a solution of 1-hydroxy-2-(1-sulphonaphth-2-ylazo)-8-(4,6-dichloro-s-triazin-2-yl) aminonaphthalene-3,6-disulphonic acid (0.01M). After 3 hours the reaction was essentially complete, as judged by thin layer chromatography, and brine (30 g, 15% w/v) was added. The title product precipitated as a solid and was collected and dried.

Yield 14.8 g, M.I. 1703, 87%, lambda max 547 nm.

The product was applied to cotton by printing and exhaust dyeing. In both cases excellent fixation was achieved resulting in heavy bluish-red shades with good fastness properties.

EXAMPLE 9

Preparation of a dye of Formula (14) wherein $D^2$ is 1-hydroxy-2-(2-sulphophenylazo)-3,6-disulphon-8-yl 2-Amino-4-(2,6-difluoro-3,5-dichloropyrid-4-ylamino)benzene sulphonic acid (0.0375M) was added to a solution of 1-hydroxy-2-(2-sulphophenylazo)-8-(4,6-dichloro-s-triazin-2-ylamino)napthalene-3,6-disulphonic acid (0.034M) in water (400 ml). The solution was stirred at pH 6.5 at 20° C. for 2 hours, a trace of insoluble material was filtered off and salt (56 g, 14% w/v) was added carefully, with stirring, to the filtrate. The resultant precipitated was collected.

Yield 35 g, M.I. 1420 72%.

Mass spectrum. Isotopic cluster (3Cl, 4S) at m/z 982 corresponding to (M-H)− together with sodium salts at m/z 1004 and 1026.

EXAMPLE 10

Preparation of a dye of Formula (14) wherein $D^2$ is 3-ureido-4-(3,6,8-trisulphonaphth-2-ylazo)phenyl A neutral aqueous solution of the sodium salt of 3-ureido-4-(3,6,8-trisulphonaphth-2-ylazo)aniline (0.02M) was added slowly, at 0° C. to 5° C., to a stirred finely divided suspension of cyanuric chloride (9.1 g) in acetone, ice and water. After 2 hours a small amount of insoluble material was filtered off and 2-amino-5-(2,6-difluoro-3,5-dichloropyridin-2-ylamino)benzene sulphonic acid was added to the solution. This was heated to 60° C. for 4 hours. On cooling salt was added (10% w/v) and the precipitated product collected and dried.

Yield 14 g, M.I. 1298.

Mass spectrum. Isotopic cluster (3Cl, 4S) at 1024, corresponding to (M-H)− together with its Na salts at 1046 and 1068 were detected, consistent with the title structure.

EXAMPLE 11

Preparation of to destroy any excess nitrous acid. A solution of 1-amino-8-hydroxynaphthalene-3,6-disulphonic acid (4.68 g, 0.012M) was added at pH 7 and 0°-5° C. The reaction proceeded at 0°-5° C., pH 2, until half of the diazonium salt had been consumed (0.02M). The pH was slowly raised to 6.5 and the remaining half of the diazonium salt consumed. The solution was allowed to warm to room temperature. Salt was added (10%) and the resultant precipitated title product collected.

Yield 7 g, M.I. 2145, 27.2%.

The product was applied to cotton by exhaust dyeing and gave a navy shade. The structure examined by negative ion FAB mass spectography showed isotopic clusters (4Cl, 2S) at m/z 1078 corresponding to (M-H)− together with sodium salts at 1100 and 1122 consistent with the desired structure.

EXAMPLE 12

Preparation of

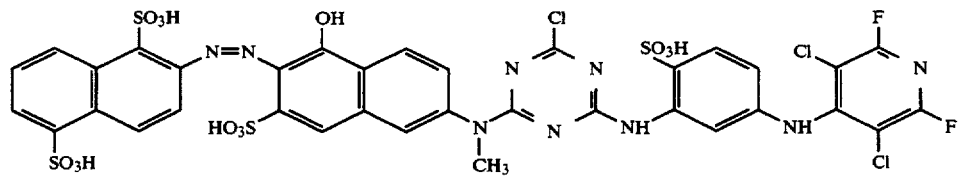

Cyanuric chloride (5 g) dissolved in acetone (50 ml) was added to a stirred mixture of 2-amino-4-(2,6-difluoro-3,5-dichloropyridin-4-yl) aminobenzene sulphonic acid (0.025M) in water and ice. The mixture was maintained at pH 6.5 by adding 2N sodium carbonate solution until the reaction was complete as judged by thin layer chromatography. After filtering off a small quantity of insoluble material the cold solution was added to a solution of 1-hydroxy-2-(1,5-disulphonaphth-2-ylazo)-6-methylaminoaphthalene-3-sulphonic acid (0.02M) and the resultant mixture heated at 55° C. and pH 6.5 for 2 hours. When the reaction was complete the mixture was allowed to cool to room temperature and the product precipitated by the addition of methylated spirits.

Yield 18 g, M.I. 1255.

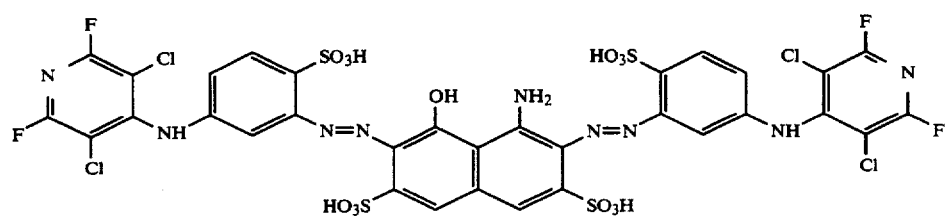

2-Amino-4-(2,6-difluoro-3,5-dichloropyridin-4-yl)aminobenzene sulphonic acid (15.36 g, 0.044M) was added to a stirred mixture of water (100 g), ice (50 g) and concentrated HCl (0.2M) followed by 2N sodium nitrite (22 ml, 0.044M). After stirring at 0° C. for 90 minutes a few drops of 10% sulphamic acid were added Mass spectrum. Isotopic cluster (3Cl, 4S) at m/z 1046 (M-H)− together with Na salts at m/z 1068, 1090 and 1112.

EXAMPLE 13

Preparation of

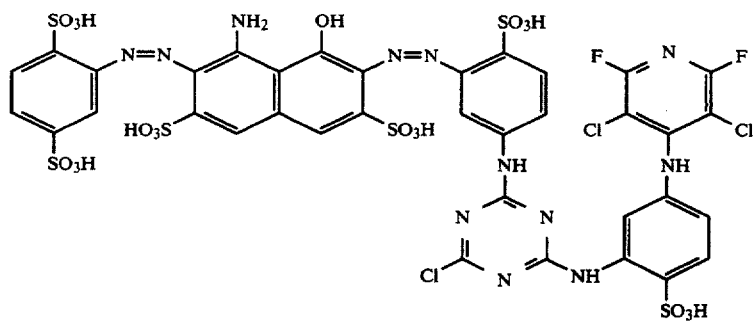

Cyanuric chloride (4.1 g) in acetone (40 ml) was added to a stirred mixture of ice/water (250 ml) and Calsolene oil (5 drops). To the resultant finely divided suspension a solution of 1-amino-2-(2,5-disulphophenylazo)-7-(2-sulpho-5-aminophenylazo)-8-hydroxynaphthalene-3,6-disulphonic acid was added slowly keeping the pH between 6 and 7 and the temperature below 5° C. After 30 minutes the mixture was passed through filter paper, the filtrate collected and 2-amino-5-(2,6-difluoro-3,5-dichloropyridin-4-ylamino)benzene sulphonic acid (0.022M) was added. The mixture was heated at 60° C. for 4 hours, cooled to 20° C., a small amount of insoluble material was filtered off and the filtrate evaporated to small volume under reduced pressure. Acetone was added to and resultant solid collected, washed and dried.

Yield 40 g, M.I. 2964.

Mass spectrum. Ions at m/z 1261 (M-H)⁻, 3Cl, 6S together with Na salts at m/z 1283, 1305 and 1327.

EXAMPLE 14

Preparation of

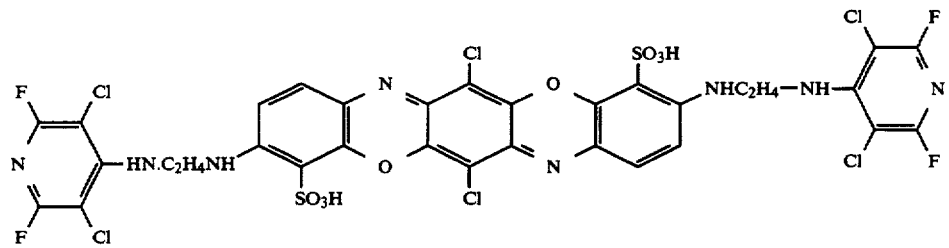

3,10-Bis-(2-aminoethylamino)-6,13-dichlorotriphenodioxazine-4,11-disulphonic acid (0.01M) was added to a solution of N,N-diethylamino ethanol (0.55M) in dimethylsulphoxide (100 ml) followed by 2,4,6-trifluoro-3,5-dichloropyridine (0.022M). After stirring at 40° C. for 2 hours the reaction was essentially complete, the mixture was drowned out onto water (750 ml) and solid collected. The crude product was slurried with acetone, collected and dried.

Yield 10 g.

The product was organically essentially pure, as judged by hplc, was examined by Nmr and negative ion fast atom bombardment mass spectrometry. An isotopic cluster consistent with the expected structure (6Cl, 2S) at m/z 991 (M-H)⁻ was detected.

I claim:

1. A water-soluble dye which contains a group of Formula (3):

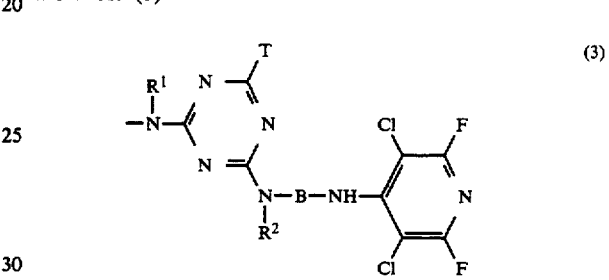

wherein:

$R^1$ & $R^2$ are each independently H or $C_{1-4}$-alkyl;

T is a labile atom or group; and

B is an optionally substituted alkylene, phenylene or naphthylene group.

2. A dye according to claim 1 wherein T is a halogen atom, a quaternary ammonium group or an optionally substituted pyridinium group.

3. A water-soluble azo, anthraquinone, phthalocyanine, triphenodioxazine or formazan dye which contains a group of Formula, (3), as defined claim 1.

4. A water-soluble dye of the formula D—$(Z)_n$ wherein Z is of Formula, or (3) as defined in claim 1, n is 1, 2 or 3 and D is the residue of an azo, anthraquinone, phthalocyanine, triphenodioxazine or formazan chromophore.

5. A process for the coloration of a substrate comprising applying thereto a dye according to any one of claims 1 to 6.

* * * * *